US00PP35420P2

(12) United States Plant Patent
Hanes

(10) Patent No.: US PP35,420 P2
(45) Date of Patent: Oct. 10, 2023

(54) ***CALIBRACHOA* PLANT NAMED 'CBRZ0046'**

(50) Latin Name: *Calibrachoa hybrida*
Varietal Denomination: CBRZ0046

(71) Applicant: SYNGENTA CROP PROTECTION AG, Basel (CH)

(72) Inventor: Mitchell E. Hanes, Morgan Hill, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/969,837

(22) Filed: Oct. 20, 2022

(51) Int. Cl.
*A01H 5/02* (2018.01)
*A01H 6/82* (2018.01)

(52) U.S. Cl.
USPC ..... Plt./413

(58) Field of Classification Search
USPC ..... Plt./413
CPC ... A01H 5/02; A01H 5/00; A01H 6/82; A01H 6/821
See application file for complete search history.

(56) References Cited

U.S. PATENT DOCUMENTS

PP23,232 P2 * 11/2012 Sakazaki ..... A01H 6/821 Plt./413

OTHER PUBLICATIONS

Germania DGI Propagators 2023 retrieved on Jan. 4, 2023 at http://204.11.17.8/orderforms/2023/dgi_727_2023.pdf, pp. 1-3, 6. (Year: 2023).*
Government of Canada Plant Breeder's Right Application 2022 retrieved on Jan. 4, 2023 at https://inspection.canada.ca/english/plaveg/pbrpov/cropreport/cal/app00012822e.shtml, 2 pp. (Year: 2022).*
Syngenta Flowers Callie Hot Pink Spark, retrieved on Jan. 4, 2023 at https://www.syngentaflowers-us.com/product/flower/70075995, 2 pp. (Year: 2023).*
Trademark Electronic Search System for Superbells retrieved on Jan. 4, 2023 at https://tmsearch.uspto.gov/bin/showfield?f=doc&state=4806:lvagxy.2.5, 2 pp. (Year: 2023).*

* cited by examiner

*Primary Examiner* — June Hwu
(74) *Attorney, Agent, or Firm* — Dale Skalla

(57) ABSTRACT

A new *Calibrachoa* plant named 'CBRZ0046' particularly distinguished by medium to big sized pink flowers with a yellow star towards the base of the petals, medium early flowering, mounding to semi-trailing plant habit, and medium vigor.

1 Drawing Sheet

Latin name of the genus and species of the plant claimed: *Calibrachoa hybrida.*

Varietal denomination: 'CBRZ0046'.

BACKGROUND OF THE NEW PLANT

The present invention comprises a new *Calibrachoa*, botanically known as *Calibrachoa hybrida*, and hereinafter referred to by the variety name 'CBRZ0046'.

'CBRZ0046' is a product of a planned breeding program. The new cultivar has medium to big sized pink flowers with a yellow star towards the base of the petals, is medium early flowering, has a mounding to semi-trailing plant habit, and is medium vigorous.

'CBRZ0046' originated from a hybridization made in May 2015 in a greenhouse in Gilroy, Calif. The female parent was an unpatented non-commercial variety 'CAL4134-1V' with pink color without yellow star towards the base of the petal, is later flowering and has a fading color when the flower ages.

The male parent of 'CBRZ0046' was an unpatented proprietary plant known as '3048-1V' having a purple flower color with yellow star towards the base of the petals, is earlier flowering and has a strong vigor.

The resulting seeds were sown in September 2015 and 'CBRZ0046' was selected as one flowering plant within the progeny of the stated cross in December 2015 in a controlled environment in Gilroy, Calif.

The first act of asexual reproduction of 'CBRZ0046' was accomplished when vegetative stem cuttings were propagated from the initial selection in January 2016 in a controlled environment in Gilroy, Calif.

BRIEF SUMMARY OF INVENTION

Horticultural examination of plants grown from cuttings of the plant initiated in the spring of 2016, and continuing thereafter, has demonstrated that the combination of characteristics as herein disclosed for 'CBRZ0046' are firmly fixed and are retained through successive generations of asexual reproduction.

'CBRZ0046' has not been observed under all possible environmental conditions. The phenotype may vary significantly with variations in environment such as temperature, light intensity, and day length.

A Plant Breeder's Right for this cultivar was applied for in Canada on Oct. 21, 2022 and assigned No. 22-11109. 'CBRZ0046' has not been made publicly available prior to the effective filing date of this application, notwithstanding any disclosure that may have been made less than one year prior to the effective filing date of this application by the inventor or another who obtained 'CBRZ0046' directly from the inventor.

The following traits have been repeatedly observed and are determined to be basic characteristics of the new variety.

The combination of these characteristics distinguishes this *Calibrachoa* as a new and distinct variety.

BRIEF DESCRIPTION OF THE PHOTOGRAPHS

The accompanying photographic drawings show typical flower and foliage characteristics of 'CBRZ0046' with colors being as true as possible with an illustration of this type.

Figure 1:
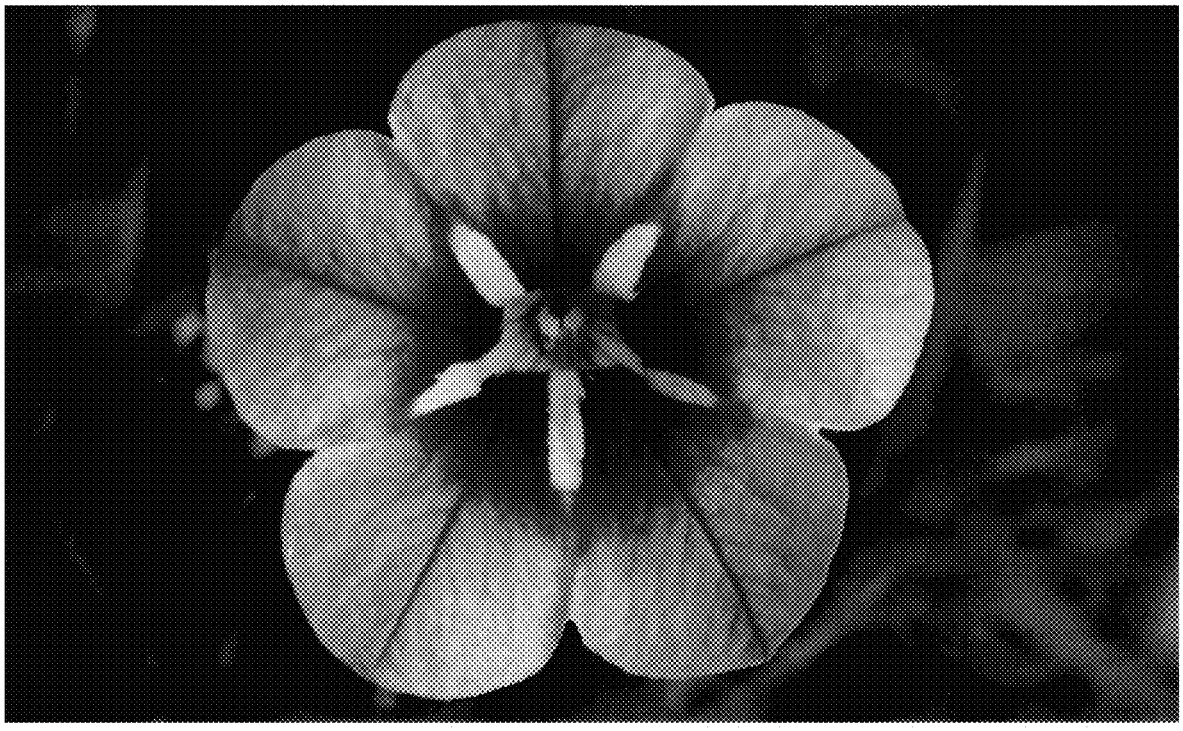

The photographic drawings show in FIG. 1 a close-up of the flowers and in

Figure 2:
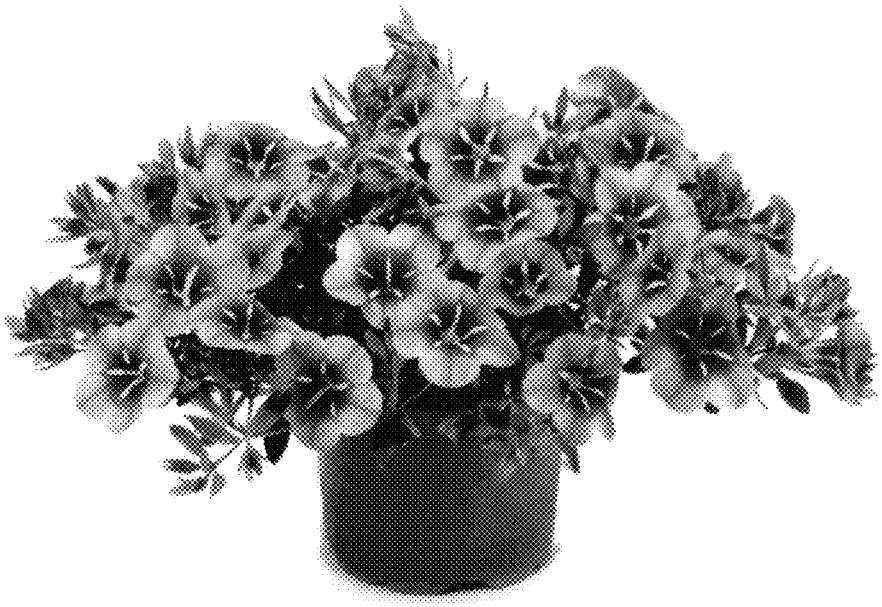

FIG. 2 a flowering plant of the new variety.

DETAILED BOTANICAL DESCRIPTION

The aforementioned photographs were taken in September 2021 in a greenhouse in Andijk, The Netherlands.

The measurements and observations were made in September 2022 in Andijk, The Netherlands on plants grown outdoor in 35 cm containers. Plants were about 16 weeks of age.

Color references are made to The Royal Horticultural Society Colour Chart (RHS) 2015.

TABLE 1

DIFFERENCES BETWEEN THE NEW VARIETY 'CBRZ0046' AND A SIMILAR VARIETY

| | 'CBRZ0046' | 'Superbells cherry star' ™ ('USCAL91001', U.S. Plant Pat. No. 23,232) |
|---|---|---|
| Flower color: | Pink color with yellow, star shaped center | Pink color, star not only in center of flower but until margin of flower |
| Vigor: | Medium vigor | Vigorous |
| Plant habit: | Mounding to semi trailing habit | Semi trailing to trailing |

Plant:

*Form, growth and habit.*—Moderately compact and mounding, very well branched.

*Plant height.*—17 cm.

*Plant height (inflorescence included).*—19 cm.

*Plant width.*—39 cm.

*Quantity of main branches.*—12-17.

*Quantity of secondary branches.*—4-6 per basal branch.

*Time to produce a flowering plant.*—9-10 weeks for a 12 cm pot (from planting of rooted cuttings).

Roots:

*Number of days to initiate.*—18-21 days at about 22° C.

*Number of days to produce a rooted cutting.*—21-24 days at 22° C.

*Type.*—Fibrous.

*Color.*—RHS 158D.

Stem:

*Color of stem.*—RHS 146B.

*Length of stem.*—Approximately 15 cm.

*Diameter.*—0.2 cm.

*Length of internodes.*—1.5-2.5 cm.

*Texture.*—Smooth, hairless.

Foliage:

*Immature leaf, color of upper surface.*—RHS 147A.

*Immature leaf, color of lower surface.*—RHS 147B.

*Mature leaf, color of upper surface.*—RHS 147A.

*Mature leaf, color of lower surface.*—RHS 147B.

*Leaf blade, length.*—3.0 cm.

*Leaf, width.*—1.4 cm.

*Shape.*—Elliptical.

*Base shape.*—Attenuate.

*Apex shape.*—Obtuse.

*Margin.*—Entire.

*Texture.*—Hairless.

*Color of veins, upper surface.*—RHS 146B.

*Color of veins lower surface.*—RHS 146B.

*Petiole color.*—RHS 146B.

*Petiole length.*—0.0-0.1 cm.

*Diameter of petiole.*—0.2 cm.

*Texture.*—Smooth.

Inflorescence:

*Type.*—Flowers solitary in upper leaf axis and slanting upright or outwards.

*Quantity of inflorescences per plant.*—Approximately 70.

*Lastingness of individual flowers.*—About 7-9 days.

*Fragrance.*—None.

*Duration of flowering.*—Continuous flowering throughout the summer.

Pedicel:

*Color of pedicel.*—RHS 146B.

*Length of pedicel.*—1.5-2.3 cm.

*Diameter of pedicel.*—1.0 mm.

*Texture of pedicel.*—Smooth, hairless.

Flower:

*Immature flowers, corolla upper surface.*—RHS 73A, towards base RHS 61B with stripes RHS12A.

*Immature flowers, corolla lower surface.*—RHS 73A.

*Mature flowers, color upper surface.*—RHS 73A, towards base RHS 59A with stripes RHS12A.

*Mature flowers, color lower surface.*—RHS 73A.

*Flower horizontal diameter.*—3.7 cm.

*Flower height (vertical).*—1.7 cm.

*Corolla tube length.*—About 1.3 cm.

*Petal apex shape.*—Rounded.

*Margin.*—Entire.

*Waviness of petals.*—Weak.

*Petal lobation.*—Moderate.

*Corolla texture.*—Smooth.

*Corolla tube color inside.*—RHS 12A with veins RHS N77B.

*Corolla tube color outside.*—RHS 1B with veins RHS152B.

*Conspicuousness of the corolla vein.*—Weak to moderate conspicuousness of veins. Color of veins N77B.

*Conspicuousness of the veins on the inner corolla tube.*—Moderate.

Bud (just before opening):

*Color at apex.*—RHS N78A.

*Length.*—2.3 cm.

*Width (upper end).*—0.7 cm.

*Shape.*—Oblong.

Calyx:

*Number of sepals.*—5.

*Color of sepals, adaxial or upper surface.*—RHS 147A.

*Color of sepals, abaxial or lower surface.*—RHS 147B.

*Length of sepals.*—14 mm.

*Width of sepals.*—3 mm.

*Sepal shape.*—Lanceolate.

*Apex shape.*—Acute.

*Margins.*—Entire.

*Texture.*—Smooth.

Reproductive organs:

*Pistil.*—1.

*Length.*—1.3 cm.

*Style color.*—RHS 145C.

*Style length.*—0.8-0.9 cm.

*Stigma color.*—RHS N144C.

*Number of stamens.*—5.

*Color of filaments.*—RHS 4D.

*Length filaments.*—0.9 cm.

*Color of pollen.*—RHS 14C.

*Pollen amount.*—Abundant.

*Fertility/seed set.*—Not observed on this hybrid.

*Disease/pest resistance.*—Not observed on this hybrid.

What is claimed is:

1. A new and distinct variety of *Calibrachoa* plant named 'CBRZ0046', substantially as illustrated and described herein.

* * * * *